(12) United States Patent
Chen et al.

(10) Patent No.: US 6,222,067 B1
(45) Date of Patent: Apr. 24, 2001

(54) ALKYLATED DIAMINOBENZENE SULFONIC ACIDS

(75) Inventors: Keh-Loong Chen, Taoyuan Hsien; Ta-Chung Yin, Taiepi, both of (TW)

(73) Assignee: Everlight USA, Inc., Pineville, NC (US)

( * ) Notice: Subject to any disclaimer, the term of this patent is extended or adjusted under 35 U.S.C. 154(b) by 0 days.

(21) Appl. No.: 09/500,016

(22) Filed: Feb. 8, 2000

(51) Int. Cl.[7] .................................................. C07C 309/00
(52) U.S. Cl. ............................................................. 562/55
(58) Field of Search .................................................. 562/55

(56) References Cited

FOREIGN PATENT DOCUMENTS

0113941 * 9/1900 (DE) .
0712906 * 5/1996 (EP) .

* cited by examiner

*Primary Examiner*—Gary Geist
*Assistant Examiner*—John N Calve
(74) *Attorney, Agent, or Firm*—Bacon & Thomas

(57) ABSTRACT

A compound of the following formula (I):

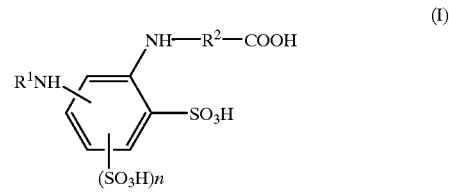

wherein $R^1$ is hydrogen or $C_{1-7}$ acyl, $R^2$ is $C_{1-3}$ alkylene, n is 0 or 1. Novel dyestuff intermediates of formula (I) compound of the present invention can be used to synthesis many kinds of dyestuffs. Also disclosed is a process for the preparation of compound of formula (I).

11 Claims, No Drawings

ALKYLATED DIAMINOBENZENE SULFONIC ACIDS

FIELD OF THE INVENTION

The present invention relates to a novel dyestuff intermediates.

BACKGROUND OF THE INVENTION

Synthetic dyestuffs have a history of more than a hundred years. In recent years few novel dyestuff intermediates have been developed. In fact the study of novel dyestuff intermediates is very important. For example, a novel dyestuff intermediate can be used to improve a manufacturing process or to synthesize a novel dyestuff.

SUMMARY OF THE INVENTION

The present invention relates to novel alkylated diaminobenzene sulfonic acid compounds of the following formula (I):

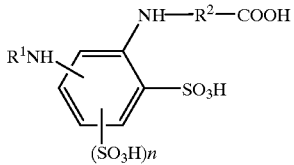

wherein $R^1$ is hydrogen or $C_{1-7}$ acyl; $R^2$ is $C_{1-3}$ alkylene, such as methylene (—$CH_2$—), ethylene (—$CH_2CH_2$—) or methylethylene (—$CH_2CH(CH_3)$—); n is 0 or 1.

The alkylated diaminobenzene sulfonic acid compounds of the formula (I) of the present invention are a novel dyestuff intermediates. They can be used to synthesize fiber reactive dyestuffs. The fiber reactive dyestuffs can be widely applied to dyeing a great range of spun and woven products that contain a hydroxyl group or amide group, etc., such as wool, silk, polyamide, and natural or synthetic fiber; and also cellulose fiber like cotton, linen, artificial cotton, and artificial linen, etc.

The present invention also relates to a process for the preparation of compounds of formula (I). The operating procedures are easy and have the advantages of high production rates and high purity.

DESCRIPTION OF THE PREFERRED EMBODIMENTS

The preparation of compounds of formula (I) compound of the present invention is described below:

A diaminobenzene sulfonic acid compound of formula (II) is acylated to obtain a monoacyl compound of formula (III)

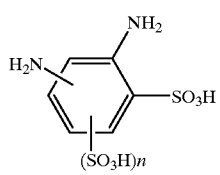

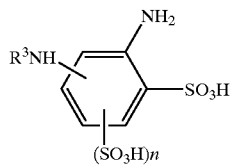

wherein n is 0 or 1; $R^3$ is $C_{1-7}$ acyl.

Regarding the acylation reaction of diaminobenzene sulfonic acids of formula (II), it can be carried out processed in aqueous solution or in organic solvent. The acylating reagent used in the reaction is a carboxylic acid derivative, such as an acid anhydride, acid chloride, or a mixture thereof. Preferred examples of acylating agents are acetic anhydride, propionic anhydride, formic anhydride, benzoic anhydride, maleic anhydride, succinic anhydride, chloroacetic anhydride, chloropropionyl chloride or benzoyl chloride; among them acetate anhydride is the most popular acylation reagent.

In the above acylation reaction of diaminobenzene sulfonic acid compound of formula (II), each mole of compound of formula (II) compound requires more than one mole of acylation reagent. More preferably 1.0–1.5 mole of acylation reagent, and most preferably 1.05–1.15 mole of acylation reagent is used. The reaction temperature of the above acylation reaction is controlled between 10° C. and 45° C., and more preferably is between 20° C. and 40° C. The pH value of the above acylation reaction is controlled between 1–10, and more preferably is between 4–6. The monoacyl compound of formula (III) can be isolated from the reaction or it is possible to proceed directly to the alkylation reaction in the next step.

The monoacyl compound of formula (III) is then reacted with an alkylation reagent that contains a carboxylic acid group to yield a compound of formula (IV) which is the compound of formula (I) of the present invention,

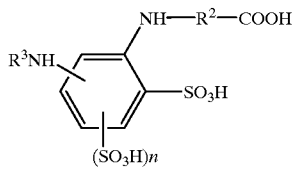

wherein n is 0 or 1; $R^2$ is $C_{1-3}$ alkylene and $R^3$ is $C_{1-7}$ acyl.

The alkylation reaction is carried out by reacting a monoacyl compound of formula (III) with an alkylating agent. The alkylating agent contains a carboxylic acid group and 2–4 carbon atoms. Examples include chloroacetic acid or 2-chloropropionic acid. Unsaturated carboxylic acids such as acrylic acid or methacrylic acid can also be used as alkylating agents. For each mole of monoacyl compound of formula (III) it is necessary to use more than one mole of alkylation reagent, preferably, 1–10 mol, and more preferably, 1.1–2.5. The reaction temperature of the alkylation reaction is controlled between 70° C. and 110° C., and, more preferably between 80° C. and 100° C. The pH value is generally controlled between 3–7, preferably between 4–6. Reaction is best carried out in presence of a catalyst such as acid, alkali or potassium iodide; the compound of formula (IV) described previously can thus be obtained.

The compound of formula (IV) can be deacylated to yield a compound of formula (V) (i.e. formula (I) of this invention, in which R1 is hydrogen).

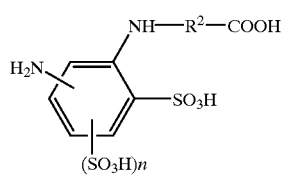

(V)

wherein n and $R^2$ are defined as stated previously.

The acylation of compound (IV) is carried out in aqueous medium. The reaction temperature is controlled between 70° C. and 110° C., and, more preferably, between 80° C. and 100° C. The pH value is controlled either above 10 or below 2. After the reaction is complete, the product is precipitated by acidifying the resultant solution, by salting out or by a combination of both to obtain the component of formula (V).

The present invention is demonstrated in more detail with reference to the following examples, which are only illustrative and are not intended to limit the scope of the present invention.

In these examples, the compound is represented by free acid, but its actual form can be as a salt, or more possibly alkali metal salt, especially sodium salt. In these examples, parts and % are counted by weight, and the temperature is Celsius ° C.

EXAMPLE 1

11.5 g of 2-amino-4-acetylaminobenzene sulfonic acid and 14.4 g of acrylic acid were mixed inside a reaction vessel: 25.0 g of aqueous sodium hydroxide (15%) were added and the mixture maintained at 80° C. and 85° C. until reaction was compete.

The mixture was allowed to cool down to room temperature and unreacted acrylic acid was removed by extraction. The aqueous layer was concentrated under reduced pressure to suitable volume and then stirred with diethyl ether while adding isopropyl alcohol; the resulting precipitated product was collected.

14.5 g of 2-β-carboxyethylamino-4-acetylamino benzene sulfonic acid, which has structure as the following formula (1):

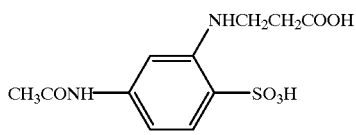

(1)

Melting point is from 249° C. to 251° C. $^1$H NMR ($D_2O$); δ=2.1(3H), 2.4(2H), 3.3(2H), 6.7(1H), 6.9(1H), 7.5(1H) ppm.

EXAMPLE 2

12.0 g of 2-β-carboxy ethylamino-4-acetylamino benzene sulfonic acid inside reactor was dissolved in 30 g of water. 45 wt % of sodium hydroxide was added to adjust the pH value of the solution to 12–13. The temperature was raised to between 95° C. and 100°0C. and the mixture stirred until reaction was complete.

After allowing the mixture to cool to room temperature. 32 wt % of hydrochloric acid was added with stirring until the pH value reached 2–3.

The precipitated product was collected under and dried at atmospheric pressure to obtain 8 g of 2-β-carboxy ethylamino-4-acetylamino benzene sulfonic acid, which has structure as the following formula (2):

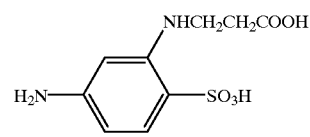

(2)

Melting point is from 240° C. to 242° C. HPLC purity is 90%; $^1$H NMR ($d^6$-DMSO); 67 =2.5(2H), 3.3(2H), 6.4(1H), 6.5(1H), 7.5(1H) ppm.

EXAMPLE 3

11.5 g of 2-amino-4-acetylamino benzene sulfonic acid (11.5 g) and 4.7 g of chloroacetic acid were dissolved in 30 g of water. After stirring for 30 s, 4.2 g of potassium iodide and 45 wt % of sodium hydroxide were added to give a pH value of between 3.5–4. After stirring the mixture at 80° C. to 85° C. for one hour the mixture was cooled and hydrochloric acid was added to pH 0 to pH 1.2-Carboxylymethylamino-4-acetylamino benzene sulfonic acid (3) was precipitated.

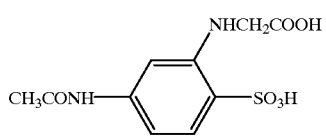

(3)

EXAMPLE 4

After filtering off the carboxymethylamino-4-acetylamino benzene sulfonic acid of Example 3, 45 wt % of sodium hydroxide (45 %) was added to give a pH value 12–13,the temperature was raised to 95° C.–100° C. and the solution was stirred until reaction was complete.

After cooling to room temperature hydrochloric acid (32 wt %) was added to pH 1–2 to precipitate the product.

After filtering off the product, it was dried under atmospheric pressure and 60° C. to yield 7.6 g of 2-carboxy methylamino-4-acetylamino benzene sulfonic acid, formula (4) below:

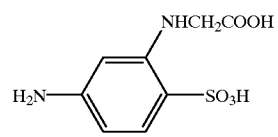

(4)

Melting point 234° C. to 235° C. HPLC purity is 97 %; $^1$H NMR($d^6$-DMSO); δ=3.9(2H), 6.3(1H), 6.4(1H), 6.5(1H), 7.5(1H) ppm.

Application Example 1

5.9 parts of 2-β-carboxy ethylamino-4-acetylamino benzene sulfonic acid of formula (2) was added to a 4-(2-sulfatoethylsulfonyl)benzyl diazonium chloride (prepared from 6.4 parts of 4-(2-sulfatoethylsulfonyl)aniline) and the pH value was controlled between 4.5–5.0. After completion of the reaction, sodium chloride was added with stirring are the solution precipitated product, was collected, an orange dyestuff of the formula (a), $\lambda_{max}$=471 nm. The dyestuff dyed cellulose materials an orange shade, with excellent properties.

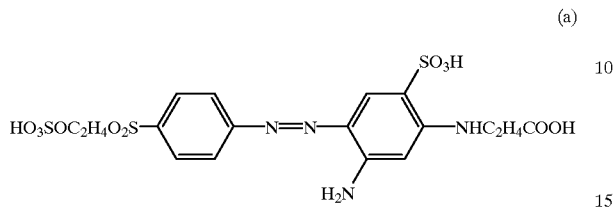

(a)

Application Example 2

Cyanuric chloride (9.32 parts) was uniformly distributed in ice water (50 parts) and a solution of 1-amino-8-hydroxynaphalene-3,6-disulphonic acid(15.97 parts), in 60 ml of water was added. The reaction temperature was maintained at 6–8 ° C., until reaction was complete. A diazonium salt of 4-(2-sulfatoethylsulfonyl)aniline (prepared from 13.77 parts of 4-(2-sulfatoethylsulfonyl) aniline) was added to the above solution. The pH value was adjusted to 6.0 and stirring was continued until reaction was complete. 2-β-carboxy ethylamino-4-acetylamino benzene sulfonic acid of the formula (2) (12.74 parts) was added to the above solution. The pH was controlled between 6–6.5 and the temperature was raised to 40° C. until reaction was complete. The diazonium salt (prepared from 14.05 parts of 4-(2-sulfatoethylsulfonyl)aniline) was added to the above solution at 5–10° C. The pH value was adjusted to 5.5–6.0. Upon completion of the reaction, the solution was desalted and dried to obtain a peach red dyestuff of formula (b), $\lambda_{max}$=502 nm. The dyestuff can be used to dye objects in peach red, with excellent fastness properties.

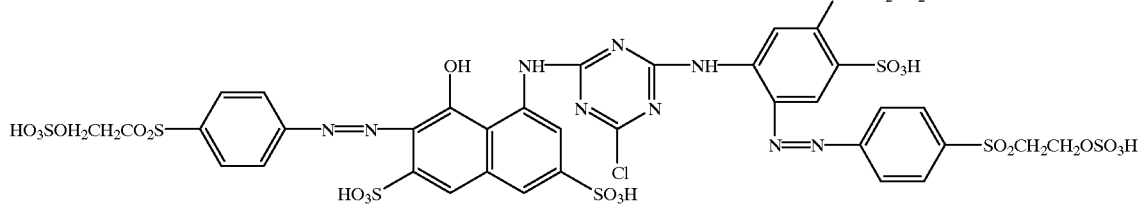

(b)

From the foregoing description, one skilled in the art can easily ascertain the essential characteristics of this invention, and, without departing from the scope thereof, can make various changes and modifications of the invention to adapt it to various usages and conditions. Thus, other embodiments are also within the claims.

What the invention claimed is:

1. A compound of the formula (I):

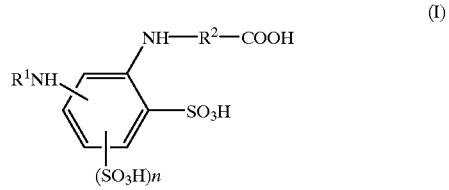

(I)

wherein:

$R^1$ is hydrogen or $C_{1-7}$ acyl;

$R^2$ is $C_{1-3}$ alkylene;

n is 0 or 1.

2. The compound of claim 1, wherein $R^2$ is methylene, 1,2-ethylene, or 1,2-propylene.

3. The compound of claim 1, wherein $R^2$ is ethylene.

4. The compound of claim 1, wherein n is 0.

5. The compound of claim 1, wherein the compound of formula (I) of is the compound of formula (I-1)

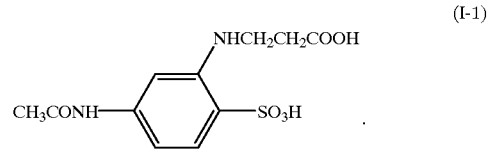

(I-1)

6. The compound of claim 1, wherein the compound of formula (I) is the compound of formula (I-2)

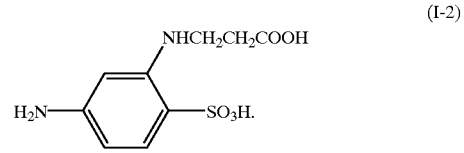

(I-2)

7. The compound of claim 1, wherein the compound of formula (I) is the compound of formula (I-3)

(I-3)

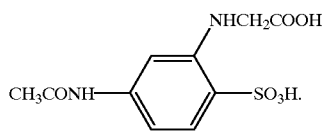

8. The compound of claim 1, wherein the compound of formula (I) compound is the compound of formula (I-4)

(I-4)

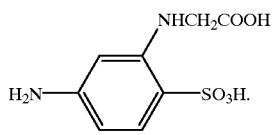

9. A process for the preparation of compound of formula (I) of claim 1, which comprises:

a) reacting a compound of the following formula (III)

(III)

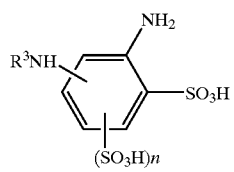

wherein n is 0 or 1; $R^3$ is $C_{1-7}$ acyl; with an alkylating agent, said alkylation reagent being selected from the group consisting of $C_{2-4}$ halo carboxylic acid or $C_{3-4}$ alkylene carboxylic acid; or b) optionally deacylating a compound of formula (IV)

(IV)

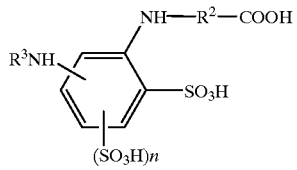

wherein n is 0 or 1; $R^2$ is $C_{1-3}$ alkylene; $R^3$ is $C_{2-5}$ acyl; to yield a compound of formula (IV) where $R^3$ is a hydrogen atom.

10. The process according to claim 9, wherein said alkylation reagent is $C_{2-4}$ halo carboxylic acid, and said alkylation reaction is conducted at a temperature of from 70° C. to 110° C., a pH value between 3 to 7, and in the presence of acid catalyst, alkali catalyst or potassium iodide.

11. The process according to claim 9, wherein said deacylation reaction is conducted in an aqueous solution, at a temperature between 70° C. and 110° C., and a pH value higher than 10 or lower than 2.

\* \* \* \* \*